United States Patent

Nappa et al.

(10) Patent No.: US 10,479,745 B2
(45) Date of Patent: Nov. 19, 2019

(54) CATALYTIC ISOMERIZATION OF Z-1,1,1,4,4,4-HEXAFLUORO-2-BUTENE TO E-1,1,1,4,4,4-HEXAFLUORO-2-BUTENE

(71) Applicant: THE CHEMOURS COMPANY FC, LLC, Wilmington, DE (US)

(72) Inventors: Mario Joseph Nappa, Leesburg, FL (US); Viacheslav A Petrov, Hockessin, DE (US); Sheng Peng, Hockessin, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 15/746,033

(22) PCT Filed: Aug. 4, 2016

(86) PCT No.: PCT/US2016/045573
§ 371 (c)(1),
(2) Date: Jan. 19, 2018

(87) PCT Pub. No.: WO2017/027323
PCT Pub. Date: Feb. 16, 2017

(65) Prior Publication Data
US 2018/0215690 A1 Aug. 2, 2018

Related U.S. Application Data

(60) Provisional application No. 62/202,382, filed on Aug. 7, 2015.

(51) Int. Cl.
*C07C 17/358* (2006.01)
*B01J 27/10* (2006.01)
*B01J 27/12* (2006.01)

(52) U.S. Cl.
CPC ............ *C07C 17/358* (2013.01); *B01J 27/10* (2013.01); *B01J 27/12* (2013.01)

(58) Field of Classification Search
CPC ....... C07C 17/25; C07C 17/358; C07C 21/18; B01J 21/04; B01J 23/26; B01J 21/066; C07B 2200/09
See application file for complete search history.

(56) References Cited

U.S. PATENT DOCUMENTS

| | | |
|---|---|---|
| 5,136,113 A | 8/1992 | Rao |
| 7,795,482 B2 | 9/2010 | Nappa et al. |
| 8,399,721 B2 | 3/2013 | Nappa et al. |
| 8,426,655 B2 | 4/2013 | Tung et al. |
| 8,436,216 B2 | 5/2013 | Sun et al. |
| 8,461,401 B2 | 6/2013 | Tung et al. |
| 8,822,739 B2 | 9/2014 | Nappa |

FOREIGN PATENT DOCUMENTS

| | | |
|---|---|---|
| FR | 2 989 374 A1 | 10/2013 |
| WO | 2015/059500 A1 | 4/2015 |
| WO | 2015/120250 A1 | 8/2015 |
| WO | 2015/142981 A1 | 9/2015 |

OTHER PUBLICATIONS

Dominique et al (FR2989374 machine translation), Preparing Hydrofluoropropene/Hydrofluorobutene in the Form of E-Isomers, Oct. 2013.*
PCT International Search Report and Written Opinion dated Oct. 18, 2016.

* cited by examiner

*Primary Examiner* — Jafar F Parsa

(57) ABSTRACT

A process is disclosed for (i) producing E-1,1,1,4,4,4-hexafluoro-2-butene (E-HFO-1336mzz) from Z-1,1,1,4,4,4-hexafluoro-2-butene (Z-HFO-1336mzz), comprising the steps of (a) providing a starting material comprising Z-1,1,1,4,4,4-hexafluoro-2-butene, (b) contacting the starting material with a suitable catalyst in a reaction zone to produce E-HFO-1336mzz; and optionally, (c) recovering the E-HFO-1336mzz. The process may be performed in the gas phase or in the liquid phase and as a batch process or as a continuous process.

28 Claims, No Drawings

CATALYTIC ISOMERIZATION OF Z-1,1,1,4,4,4-HEXAFLUORO-2-BUTENE TO E-1,1,1,4,4,4-HEXAFLUORO-2-BUTENE

FIELD

The present disclosure relates to processes for the catalytic isomerization of Z-1,1,1,4,4,4-hexafluoro-2-butene to produce E-1,1,1,4,4,4-hexafluoro-2-butene.

BACKGROUND

HFO-1,1,1,4,4,4-hexafluoro-2-butene, also known as HFO-1336mzz, or 1336mzz has performance properties suitable for use as a refrigerant or working fluid in applications such as air conditioning, chillers, heat pumps and organic Rankine cycles, as well as for use in foam applications. HFO-1336mzz has an ozone depletion potential of zero and low global warming potential which are desirable attributes for use as or in refrigerants and foam expansion agents.

HFO-1336mzz may exist as one of two configurational isomers, that is, the cis- or Z-isomer and the trans- or E-isomer. Processes to prepare HFO-1336mzz are known and produce a mixture of the two isomers. Each isomer has different properties, therefore, one isomer or the other may be preferred, depending on the use or application.

Because processes to produce HFO-1336mzz provide mixtures of isomers, there may be times when only one of the isomers is desired. In particular, there may be desire for only the E-isomer. Alternatively, there may be desire for only the Z-isomer.

WO 2015/059500 discloses a process to isomerize Z-1336mzz to E-1336mzz using a low sodium (less than 800 ppm) alumina based catalyst.

U.S. Pat. Nos. 8,426,655 and 8,461,401 disclose processes to prepare HFO-1336mzz starting from carbon tetrachloride and ethylene with addition of more carbon tetrachloride and HF. A mixture of 1336mzz isomers is produced. Therein, it is disclosed a preference for the cis- or Z-isomer. These patents disclose isomerizing E-1336mzz to Z-1336mzz in a vapor phase reactor using a catalyst selected from halogenated metal oxide, Lewis acid metal halides and zero valent metals.

There continues to be value to produce E-HFO-1336mzz.

SUMMARY

Disclosed herein is a process to produce the trans-isomer of HFO-1336mzz (E-1,1,1,4,4,4-hexafluoro-2-butene) by isomerization of the cis-isomer of HFO-1336mzz (Z-1,1,1,4,4,4-hexafluoro-2-butene).

Z-HFO-1336mzz can be isomerized to E-HFO-1336mzz by contacting with a suitable catalyst. The isomerization can be performed in the liquid phase or in the gas phase. The isomerization process can be performed as a batch process or as a continuous process. The process may be supplemented by the step of recovering the E-1,1,1,4,4,4-hexafluoro-2-butene (E-1336mzz).

The foregoing the following description are exemplary and explanatory only and are not restrictive of the invention as defined in the appended claims.

DESCRIPTION

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. If, alternatively, relative terms, such as "less than", "greater than" and the like are used to define an amount, concentration, or other value or parameter, the value recited is excluded.

1,1,1,4,4,4-hexafluoro-2-butene or HFO-1336mzz (each of which may be used herein interchangeably and are synonymous) may exist as one of two configurational isomers, E or Z, wherein E is the trans-isomer and Z is the cis isomer. HFO-1336mzz or 1336mzz as used herein refers to the isomers, E-HFO-1336mzz or Z-HFO-1336mzz, as well as any combinations or mixtures of such isomers.

E-1,1,1,4,4,4-hexafluoro-2-butene or E-HFO-1336mzz or E-1336mzz are used interchangeably and are synonymous herein and all refer to the cis isomer of 1,1,1,4,4,4-hexafluoro-2-butene.

Z-1,1,1,4,4,4-hexafluoro-2-butene or Z-HFO-1336mzz or Z-1336mzz are used interchangeably and are synonymous herein and all refer to the trans isomer of 1,1,1,4,4,4-hexafluoro-2-butene.

The present disclosure provides a process to isomerize Z-1336mzz to form E-1336mzz. The process comprises contacting Z-1336mzz with a suitable catalyst in a reaction zone to produce a product comprising E-1336mzz. This isomerization process can be carried out in the liquid phase or gas phase using well-known chemical engineering practices, which include continuous, semi-continuous or batch operations.

HFO-1336mzz may be prepared by contacting $CF_3$—$CCl$=$CCl$—$CF_3$ with hydrogen in the presence of a catalyst, for example, as disclosed in U.S. Pat. Nos. 7,795,482 and 8,399,721.

HFO-1336mzz may be prepared by contacting $CF_3$—$CHCl_2$ with copper in the presence of an amide solvent and 2,2'-bipyridine, as disclosed in U.S. Pat. No. 8,436,216.

HFO-1336mzz may be prepared by (1) contacting $CCl_3$—$CF_3$ with hydrogen in the presence of a catalyst comprising ruthenium, to produce 1316mxx (2,3-dichloro-1,1,1,4,4,4-hexafluoro-2-butene); (2) contacting 1316mxx with hydrogen in the presence of a catalyst containing copper, nickel, copper-nickel, or copper-palladium to provide E- or Z-1326mxz (1,1,1,4,4,4-hexafluoro-2-chloro-2-butene); and (3) contacting 1326mxz with an aqueous solution of an alkali metal hydroxide in the presence of a quaternary alkylammonium salt to provide a mixture comprising hexafluoro-2-butyne; and (4) contacting hexafluoro-2-butyne with hydrogen and a catalyst, as disclosed in WO 2015/120250.

HFO-1336mzz may be prepared by (1) contacting 3,3,3-trifluoro-1-propene with carbon tetrachloride to provide 2,4,4,4-tetrachloro-1,1,1-trifluorobutane; and (2) contacting 2,4,4,4-tetrachloro-1,1,1-trifluorobutane as disclosed in WO 2015/142981.

In any process to prepare HFO-1336mzz, a mixture of the Z- and E-isomers may be produced. Z-1336mzz may be separated from the mixture, for example, by distillation. Z-1336mzz produced in any method may serve as starting material for the process disclosed herein. A mixture E-1336mzz and Z-1336mzz may alternatively be used.

In some embodiments of this disclosure, a suitable catalyst for the isomerization comprises chromium. In some embodiments of this invention, the suitable catalyst comprises chromium oxyfluoride. In one embodiment, chromium oxyfluoride is represented by the formula $Cr_2O_xF_y$, wherein $x+y/2=3$. In another embodiment, chromium oxyfluoride is represented by the formula CrOF. Typically, a chromium oxyfluoride catalyst is used in a gas phase isomerization process.

A suitable catalyst comprising chromium oxyfluoride may further comprise other metals, such as, but not limited to cobalt, manganese, nickel, iron in the form of the metal, oxide, halide, oxyhalide or as other inorganic salts. Supports may be present such as $AlF_3$ or carbon.

Carbon used in the embodiments of this invention may come from any of the following sources: wood, peat, coal, coconut shells, bones, lignite, petroleum-based residues and sugar. Commercially available carbons which may be used include those sold under the following trademarks: Barneby & Sutcliffe™, Darco™, Nucharm™, Columbia JXN™, Columbia LCK™, Calgon™ PCB, Calgon™ BPL, Westvaco™, Norit™, Takeda™ and Barnaby Cheny NB™.

Embodiments of carbon include both non-acid washed and acid-washed carbons. In some embodiments of this invention, carbon may be prepared by treating the carbon with acids such as $HNO_3$, HCl, HF, $H_2SO_4$, $HClO_4$, $CH_3COOH$, and combinations thereof. Acid treatment is typically sufficient to provide carbon that contains less than 1000 ppm of ash. Some suitable acid treatments of carbon are described in U.S. Pat. No. 5,136,113.

In some embodiments of this invention, carbon is an activated carbon. In some embodiments of this invention, carbon is a non-acid washed activated carbon. In some embodiments of this invention, carbon is an acid washed activated carbon. The carbon can be in any form, such as, powder, granules, or pellets.

Chromium oxyfluoride may be prepared by any available method, such, for example, by treating chromium oxide ($Cr_2O_3$) with a fluorinating agent such as HF, $CCl_3F$, $COF_2$ or hydrofluorocarbons. Other non-limiting methods to prepare chromium oxyfluoride are known and selected methods are disclosed, for example, in U.S. Pat. No. 8,822,739, and references disclosed therein.

In some embodiments of this invention, the suitable catalyst comprises a metal-modified chromium oxide or a metal-modified chromium oxyfluoride. Typically, a metal-modified chromium oxide catalyst or a metal-modified chromium oxyfluoride catalyst is used in a gas phase isomerization process. In some embodiments of this invention, such metal is selected from the group consisting of magnesium (e.g. magnesium fluoride), Group VIIB metals (e.g., manganese), Group IIIB metals (e.g., lanthanum), and zinc. In use, such metals are normally present as halides (e.g., fluorides), as oxides and/or as oxyhalides. In some embodiments of this invention, these metals are supported on chromium oxide or chromium oxyfluoride.

In one embodiment, the reaction is performed in the liquid phase. Any liquid phase isomerization catalyst may be used. A nonexhaustive list includes Lewis acids, metal halides, metal oxides, or combinations of two or more thereof. For example, a metal halide may be a Group IVB metal halide, a Group VB metal halide, or combinations of two or more thereof.

Non-exclusive examples of liquid phase isomerization catalysts include boron halide, aluminum halide, antimony halide, tin halide, tantalum halide, titanium halide, niobium halide, molybdenum halide, iron halide, fluorinated chrome halide, or combinations thereof. Halides include fluoride, chloride, bromide, iodide. Specific non-exclusive examples of liquid phase isomerization catalysts contain $SbCl_5$, $SbCl_3$, $SbF_5$, $SnCl_4$, $TaCl_5$, $TaF_5$, $TiCl_4$, $NbCl_5$, $NbF_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. By "fluorinated species" of a metal chloride, is meant herein that one or more of the chlorine atoms in a metal chloride are replaced by fluorine atoms.

In certain embodiments, the liquid phase isomerization catalyst is or contains $BZ_3$, where each Z is independently Br, F or Cl. In certain embodiments, the liquid phase isomerization catalyst is or contains or $AlZ_3$, where each Z is independently Br, F or Cl, provided that Z cannot be entirely F.

In a particular embodiment, $AlZ_3$ has the formula $AlCl_xF_y$ (mixed aluminum halide) is an aluminum chlorofluoride, where the total number of atoms of halide, x plus y equals 3, where x ranges from about 0.05 to 2.95 and y ranges from about 2.95 to 0.05. Details of the aluminum chlorofluoride catalyst preparation are disclosed in U.S. Pat. No. 5,162,594 which is incorporated herein by reference.

In certain embodiments, the liquid phase isomerization catalyst contains $MCl_{5-n}F_n$, wherein M=Sb or Ta, where n=0-5. A catalyst containing $MCl_{5-n}F_n$, includes $MCl_{5-n}F_n$ or $MCl_{5-n}F_n$ supported on $AlF_3$ or carbon, where n=0-5. In one embodiment the catalyst is antimony pentafluoride. In one embodiment the catalyst is antimony pentachloride. In one embodiment the catalyst is tantalum pentafluoride. In one embodiment the catalyst is antimony pentachloride. Optionally, a liquid phase process may be performed in the presence of HF.

A process to isomerize Z-1336mzz comprises contacting Z-1336mzz with a suitable catalyst in a reaction zone to produce a product comprising E-1336mzz. The isomerization process can be carried out in the liquid phase or gas phase.

In one embodiment, there is provided a process for the isomerization of Z-1336mzz to E-1336mzz with a suitable catalyst in a reaction zone in the gas phase.

A suitable catalyst for use in the gas phase may be, for example, in the form of pellets, powders or granules. The form of such catalysts is not critical. Suitable catalysts are described above. For example, a suitable catalyst for use in the gas phase is a catalyst, which contains chromium. In one embodiment, a suitable catalyst comprises or is chromium oxyfluoride. In a particular embodiment, a suitable catalyst for use in the gas phase comprises or is chromium oxyfluoride.

In one embodiment a suitable catalyst for a gas phase isomerization process comprises or is chromium oxyfluoride. In certain embodiments the catalyst comprises chromium oxyfluoride and alumina, wherein the catalyst comprises less than 40% by weight alumina or less than 30% by weight alumina or less than 20% by weight alumina or less than 10% by weight alumina or less than 5% by weight alumina or less than 1% by weight alumina. A suitable chromium oxyfluoride catalyst is alumina-free.

The temperature employed in the reaction zone of a gas phase isomerization process typically ranges from about 100° C. to about 500° C. In some embodiments, the temperature employed in the reaction zone ranges from about 150° C. to about 400° C. or from about 250° C. to about 300° C.

The reaction zone pressure for a gas phase isomerization process can be subatmospheric, atmospheric or superatmospheric. In some embodiments of the invention, the reaction zone pressure can be up to 200 psig (1.4 MPa). In some embodiments of the invention, the reaction zone pressure is near atmospheric. In some embodiments of the invention, the pressure is from about atmospheric (101 kPa) to about 700 psig (4.8 MPa).

In one embodiment, there is provided a process for the isomerization of Z-1336mzz to E-1336mzz with a suitable catalyst in a reaction zone in the liquid phase.

Suitable catalysts are described above, which include Lewis acids, metal halides, metal oxides, or combinations thereof. A metal halide may be a Group IVB metal halide, a Group VB metal halide, or combinations thereof.

In one embodiment a suitable catalyst for a liquid phase isomerization process comprises aluminum halide. In particular, a suitable catalyst comprises $AlZ_3$, wherein each Z is independently Br, F, or Cl, provided Z cannot be entirely F. A suitable catalyst is $AlCl_xF_y$ (mixed aluminum halide, wherein Z is a combination of Cl and F), where the total number of atoms of halide, x plus y equals 3, where x ranges from about 0.05 to 2.95 and y ranges from about 2.95 to 0.05.

In one embodiment a suitable catalyst for a liquid phase isomerization process comprises antimony. In particular a suitable catalyst comprises $SbCl_{5-n}F_n$, wherein n=0, or n=1, or n=2, or n=3, or n=4, or n=5. In certain embodiments the suitable catalyst is or comprises $SbCl_5$.

In another embodiment a suitable catalyst for a liquid phase isomerization process comprises tantalum. In particular a suitable catalyst comprises $TaCl_{5-n}F_n$, wherein n=0, or n=1, or n=2, or n=3, or n=4, or n=5. In certain embodiments the suitable catalyst is or comprises $TaCl_5$.

In a liquid phase isomerization process as disclosed herein, the reaction zone temperature typically ranges from about −20° C. to about 150° C. In some embodiments, the reaction zone temperature ranges from about 50° C. to about 150° C. or from about 100° C. to about 130° C. In some embodiments, the reaction zone temperature ranges from about 100° C. to about 130° C. In some embodiments, the reaction zone temperature is about ambient, i.e., room temperature. The reaction zone pressure for the liquid phase isomerization process can be subatmospheric, atmospheric or superatmospheric. In some embodiments, the reaction zone pressure is near atmospheric. Typical pressure is from about atmospheric (101 kPa) to about 700 psig (4.8 MPa).

The contact time of the starting material which contains Z-HFO-1336mzz with the suitable catalyst for a gas phase isomerization process or a liquid phase isomerization process, either of which can be a batch or continuous process, can vary widely depending on the degree of conversion desired and generally will be from about 1 second to about 120 seconds.

In one embodiment of a gas phase isomerization process as disclosed herein, the process is a batch process with a contact time from about 1 second to about 120 seconds. In one embodiment of a gas phase isomerization process as disclosed herein, the process is a continuous process with a contact time from about 1 second to about 120 seconds.

In one embodiment of a liquid phase isomerization process as disclosed herein, the process is a batch process with a contact time from about 1 second to about 120 seconds. In one embodiment of a liquid phase isomerization process as disclosed herein, the process is a continuous process with a contact time from about 1 second to about 120 seconds.

It will be understood, that contact time in the reaction zone is reduced by increasing the flow rate of the starting material into the reaction zone.

In an embodiment, the process for isomerizing Z-1,1,1,4,4,4-hexafluoro-2-butene to E-1,1,1,4,4,4-hexafluoro-2-butene, "the isomerization process", is conducted as a batch process in the gas phase or in the liquid phase.

In an embodiment, the isomerization process is conducted in a continuous process in the gas phase or in the liquid phase. In one embodiment, the isomerization process is conducted in a continuous process in the gas phase. In one embodiment, the isomerization process is conducted in a continuous process in the liquid phase.

In certain embodiments of a continuous process, the starting material is Z-1336mzz or a mixture of Z-1336mzz and E-1336mzz. In one embodiment, the starting material is Z-1336mzz. In one embodiment, the starting material comprises Z-1336mzz. In one embodiment, the starting material comprises Z-1336mzz and E-1336mzz. The starting material is passed through a reaction vessel containing the catalyst. The reaction vessel can be any time of closed vessel such as, for example, a metal tube. In a gas phase process, the reaction vessel may be packed with the catalyst to form the reaction zone.

The conditions of the reacting step, including the choice of catalyst, are selected to obtain E-1,1,1,4,4,4-hexafluoro-2-butene at a selectivity of at least 85%, or at least 90%, or at least 95%.

In some embodiments of this invention, isomerization yield of E-1336mzz is at least 90 mole %. In some embodiments of this invention, isomerization yield of E-1336mzz is at least 95 mole % or at least 99 mole %.

In one embodiment, upon completion of a batch-wise or continuous isomerization process, the E-1336mzz can be recovered through any conventional process, including for example, fractional distillation. In another embodiment, upon completion of a batch-wise or continuous hydrogenation process, the E-1336mzz is of sufficient purity to not require further purification steps.

In certain embodiments, there is unreacted Z-1336mzz in the product. In one such embodiment, unreacted Z-1336mzz can be separated from the product and recycled to the reaction zone for the production of additional E-1336mzz.

The reaction vessel (reactors), distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The various embodiments of each reaction and recovery described above can be used in any combination in the integrated process of the present invention.

EXAMPLES $SbF_5$, $SbCl_5$, $TaCl_5$ are available from Sigma Aldrich, St. Louis, Mo. Hydrogen fluoride was purchased from SynQuest Labs, Inc., Alachua, Fla.

Examples 1-4. Liquid Phase Isomerization of Z-1336mzz to E-1336mzz Using $SbCl_5$ or $TaCl_5$ Catalyst Catalyst, $SbCl_5$ (5 g, 0.016 mol) or $TaCl_5$ (6.15 g, 0.016 mol) was added into a 210 mL Hastelloy C reactor, followed by HF addition (20 g, 1 mol). The reaction mixture was heated to 100° C. for 1 hour and cooled to 0° C. Z-1336mzz (30 g, 0.18 mol) was added and the vessel and the reaction as heated back to 100° C. for 20 hours. 50 g ice water was added to quench the reaction. The product was analyzed by GC.

Results are summarized in Table 1.

TABLE 1

| Liquid Phase Isomerization Results | | | | |
|---|---|---|---|---|
| | Example # | | | |
| | 1 | 2 | 3 | 4 |
| Z-1336mzz | 30 g (0.18 mol) | 30 g (0.18 mol) | 30 g (0.18 mol) | 30 g (0.18 mol) |
| HF | 20 g (1 mol) | 20 g (1 mol) | 20 g (1 mol) | 20 g (1 mol) |
| $SbCl_5$ | 5 g (0.016 mol) | | | |
| $TaCl_5$ | | 6.15 (0.016 mol) | 6.15 (0.016 mol) | 6.15 (0.016 mol) |
| Temperature (° C.) | 100 | 130 | 130 | 110 |
| Time (hrs) | 20 | 20 | 10 | 20 |
| Conversion (%) | 44.6 | 96.5 | 72.5 | 75.3 |
| Selectivity to E-1336mzz (%) | 98.3 | 99.5 | 99.7 | 99.8 |
| Yield* of E-1336mzz (%) | 98.3 | 98.5 | 99.7 | 99.8 |

*Based on recovered Z-1336mzz.

Example 5. Liquid Phase Isomerization of Z-1336mzz to E-1336mzz Using $SbF_5$ Catalyst Antimony pentafluoride ($SbF_5$, 1 g) was placed in 50 mL round bottomed flask inside of a dry box. The reaction vessel was transferred into a fume hood and was equipped with thermocouple, dry ice condenser, addition funnel and magnetic stir bar. 20 g of cis-HFO-1336mzz (containing 0.3 mol % of the trans isomer) was added to reaction vessel at 0° C. over a 15 minute period, under nitrogen blanket. The reaction mixture was agitated at ambient temperature for 3 days (reaction vessel was kept at −78° C. overnight and the reaction was resumed next morning). The conversion of cis-HFO-1336mzz was monitored by GC and $^{19}F$ NMR. After 3 days (~28 hours total at ambient temperature) the ratio of cis/trans was found to be 0.4:99.6.

Example 6. Liquid Phase Isomerization of Z-1336mzz to E-1336mzz Using Aluminum Chlorofluoride Catalyst Aluminum chlorofluoride ($AlCl_xF_y$, "ACF", 0.4 g, prepared in accordance with U.S. Pat. No. 5,162,594) was placed in a 50 mL round bottomed flask inside of a dry box. The reaction vessel was transferred into a fume hood and was equipped with thermocouple, dry ice condenser, addition funnel and magnetic stir bar. 20 g of cold cis-HFO-1336mzz (containing 0.1 mol % of the trans isomer) was added to a reaction vessel at 20° C. over a 15 minute period, under nitrogen blanket.

The temperature of the reaction mixture went from 10° C. to 24° C. during the addition step. The reaction mixture was agitated at ambient temperature for 2 hours. The conversion of cis-HFO-1336mzz into the trans isomer was monitored by $^{19}F$ NMR. According NMR data the ratio of cis/trans isomers changed from 99.9:01 (starting material) to 0.6:99.4 in the crude product after 2 hours at ambient temperature.

Examples 7-9. Gas Phase Isomerization of Z-1336mzz to E-1336mzz

Catalyst Preparation and Activation

Into an Inconel® (0.5 inch OD) tube was added 6 cc of chromium oxide, formed by pressing hydrated chromic oxide powder at 30,000 lb. The resulting mass was crushed and sieved to 12/20 mesh.

The chromium oxide was converted to chromium oxyfluoride and activated as follows. The chromium oxide was heated at 300° C. under 30 cc/min of nitrogen flow for 200 minutes. Then nitrogen flow was increased to 60 cc/min and HF was introduced at 20 cc/min for 60 minutes. Then the temperature was increased to 325° C. for 300 minutes. Then the nitrogen and HF flow were each set to 30 cc/min for 30 minutes. Then nitrogen flow was lowered to 12 cc/min and HF flow was increased to 48 cc/min for 60 minutes. The nitrogen was then turned off and HF was allowed to flow at 48 cc/min. for an additional 30 minutes. The temperature of the reactor was then decreased to 250° C. for 30 minutes. After activation, the reactor was purged with nitrogen.

Run Conditions and Results

A stream of Z-1,1,1,4,4,4-hexafluoro-2-butene (Z-HFO-1336mzz) preheated at 50° C. was fed into the tube reactor. Part of the reactor effluent was passed through a series of valves and analyzed by GCMS.

In Examples 7 and 8, the catalyst was as described above. In Example 7, the gas flow rate of Z-1336mzz fed to the reactor was 9.51 standard cubic centimeters per minute ("sccm"). In Example 8, the gas flow rate of Z-1336mzz fed to the reactor was 4.75 sccm.

In Example 9 (Comparative), no catalyst was used. In Example 9, the gas flow rate of Z-1336mzz fed to the reactor was 4.75 sccm.

Reaction temperatures, feed rates and results are listed in Tables 2-4 below.

TABLE 2

Results - Example 7

| Run No. | Temp, ° C. | Mole Percent | | |
|---|---|---|---|---|
| | | Z-1336mzz | E-1336mzz | Others |
| 1 | 150 | 63.32 | 36.65 | 0.02 |
| 2 | 150 | 67.65 | 32.32 | 0.02 |
| 3 | 150 | 68.39 | 31.59 | 0.02 |
| 4 | 250 | 0.81 | 99.15 | 0.04 |
| 5 | 250 | 0.79 | 99.18 | 0.04 |
| 6 | 250 | 0.78 | 99.20 | 0.02 |
| 7 | 300 | 1.13 | 98.83 | 0.04 |
| 8 | 300 | 1.15 | 98.81 | 0.04 |
| 9 | 300 | 1.13 | 98.83 | 0.03 |

TABLE 3

Results - Example 8

| Run No. | Temp, ° C. | Mole Percent | | |
|---|---|---|---|---|
| | | Z-1336mzz | E-1336mzz | Others |
| 1 | 100 | 99.09 | 0.56 | 0.26 |
| 2 | 100 | 99.50 | 0.48 | 0.01 |
| 3 | 100 | 99.52 | 0.47 | 0.01 |
| 4 | 150 | 91.48 | 8.51 | 0.01 |
| 5 | 150 | 87.98 | 12.00 | 0.02 |
| 6 | 150 | 87.69 | 12.30 | 0.02 |
| 7 | 200 | 16.22 | 83.77 | 0.02 |
| 8 | 200 | 12.21 | 87.78 | 0.02 |
| 9 | 200 | 15.50 | 84.48 | 0.02 |

TABLE 4

Results - Example 9 (Comparative)

| Run No. | Temp, ° C. | Mole Percent | | |
|---|---|---|---|---|
| | | Z-1336mzz | E-1336mzz | Others |
| 1 | 150 | 99.82 | 0.17 | 0.01 |
| 2 | 150 | 99.89 | 0.09 | 0.01 |
| 3 | 200 | 99.92 | 0.06 | 0.01 |
| 4 | 200 | 99.94 | 0.05 | 0.01 |
| 5 | 251 | 99.94 | 0.05 | 0.02 |
| 6 | 250 | 99.93 | 0.05 | 0.01 |
| 7 | 300 | 99.92 | 0.06 | 0.01 |
| 8 | 300 | 99.94 | 0.05 | 0.02 |
| 9 | 350 | 99.83 | 0.15 | 0.01 |

What is claimed is:

1. A process for isomerizing Z-1,1,1,4,4,4-hexafluoro-2-butene to E-1,1,1,4,4,4-hexafluoro-2-butene comprising:
   (a) providing a starting material comprising Z-1,1,1,4,4,4-hexafluoro-2-butene;
   (b) contacting the starting material with a suitable catalyst in a reaction zone to produce E-HFO-1336mzz; and optionally,
   (c) recovering the E-HFO-1336mzz,
   wherein, when the contacting step is performed in the gas phase, the catalyst comprises chromium and less than 40% by weight alumina;
   wherein when the contacting step is performed in the liquid phase, the catalyst comprises a metal halide wherein the metal halide is aluminum halide, antimony halide, tin halide, tantalum halide, titanium halide, niobium halide, molybdenum halide, iron halide, fluorinated chrome halide, or combinations thereof.

2. The process of claim 1 wherein the contacting step is performed in the gas phase.

3. The process of claim 1 wherein the contacting step is performed in the liquid phase.

4. The process of claim 1 further comprising recovering the E-HFO-1336mzz.

5. The process of claim 1 wherein a suitable catalyst comprises chromium oxyfluoride.

6. The process of claim 1 wherein a suitable catalyst contains $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof.

7. The process of claim 6 wherein a suitable catalyst contains $MCl_{5-n}F_n$, wherein M=Sb or Ta and n=0-5.

8. The process of claim 7 wherein the catalyst is antimony pentafluoride.

9. The process of claim 7 wherein the catalyst is tantalum pentafluoride.

10. The process of claim 6 wherein a suitable catalyst contains $AlZ_3$, wherein Z is one or more of Br, F or Cl, provided that Z cannot be entirely F.

11. The process of claim 10 wherein $AlZ_3$ has the formula $AlCl_xF_y$, where the total number of atoms of halide, x plus y equals 3, where x ranges from about 0.05 to 2.95 and y ranges from about 2.95 to 0.05.

12. The process of claim 2 wherein the temperature in the reaction zone is in the range from about 100° C. to about 500° C.

13. The process of claim 12 wherein the temperature in the reaction zone is in the range from about 150° C. to about 400° C.

14. The process of claim 13 wherein the temperature in the reaction zone is in the range from about 250° C. to about 300° C.

15. The process of claim 3 wherein the temperature in the reaction zone is in the range of −20° C. to about 150° C.

16. The process of claim 15 wherein the temperature in the reaction zone is in the range of from about 50° C. to about 150° C.

17. The process of claim 16 wherein the temperature in the reaction zone is in the range of from about from about 100° C. to about 130° C.

18. The process of claim 1 wherein the process is a batch process.

19. The process of claim 1 wherein the process is a continuous process.

20. The process of claim 2 wherein the process is a batch process.

21. The process of claim 2 wherein the process is a continuous process.

22. The process of claim 3 wherein the process is a batch process.

23. The process of claim 3 wherein the process is a continuous process.

24. The process of claim 1 wherein the starting material comprises Z-1336mzz and E-1336mmzz.

25. The process of claim 1 wherein the yield of E-1336mzz is at least 90 mole %.

26. The process of claim 1 wherein the yield of E-1336mzz is at least 95 mole %.

27. The process of claim 1 wherein the yield of E-1336mzz is at least 99 mole %.

28. The process of claim 1 wherein there is unreacted Z-1336mzz in the product, and wherein such unreacted Z-1336mzz is separated from the product and recycled to the reaction zone.

\* \* \* \* \*